United States Patent
Alanen et al.

(10) Patent No.: US 9,271,676 B2
(45) Date of Patent: Mar. 1, 2016

(54) METHOD FOR MEASURING OF EDEMA

(75) Inventors: Esko Alanen, Savonlinna (FI); Aulis Tapani Lahtinen, Kuopio (FI); Jouni Nuutinen, Kuopio (FI)

(73) Assignee: Delfin Technologies Ltd., Kuopio (FI)

( * ) Notice: Subject to any disclaimer, the term of this patent is extended or adjusted under 35 U.S.C. 154(b) by 513 days.

(21) Appl. No.: 10/670,144

(22) Filed: Sep. 23, 2003

(65) Prior Publication Data

US 2005/0177061 A1 Aug. 11, 2005

Related U.S. Application Data

(63) Continuation-in-part of application No. PCT/FI02/00234, filed on Mar. 21, 2002.

(30) Foreign Application Priority Data

Mar. 23, 2001 (FI) .................................... 20010601

(51) Int. Cl.
*A61B 5/05* (2006.01)
*A61B 5/00* (2006.01)
*A61B 5/053* (2006.01)

(52) U.S. Cl.
CPC ............ *A61B 5/4878* (2013.01); *A61B 5/0531* (2013.01); *A61B 5/0537* (2013.01)

(58) Field of Classification Search
CPC ............ A61B 5/0537; A61B 5/4869–5/4884; A61B 5/0531–5/0533
USPC ............... 600/547, 306; 73/73; 324/689–690
See application file for complete search history.

(56) References Cited

U.S. PATENT DOCUMENTS

| | | | |
|---|---|---|---|
| 2,184,511 A | 12/1939 | Bagno et al. | 324/650 |
| 3,316,896 A | 5/1967 | Thomasset | 600/547 |
| 3,340,867 A | 9/1967 | Kubicek et al. | 600/526 |
| 3,347,223 A | 10/1967 | Pacela | 600/547 |
| 3,452,743 A | 7/1969 | Rieke | 600/547 |
| 3,608,543 A | 9/1971 | Longini et al. | 128/2.1 R |
| 3,677,261 A | 7/1972 | Day | 128/2.1 Z |
| 3,730,171 A | 5/1973 | Namon | 128/2.05 Z |

(Continued)

FOREIGN PATENT DOCUMENTS

| | | |
|---|---|---|
| EP | 1118308 A1 | 1/2001 |
| GB | 1 432 316 | 4/1976 |

(Continued)

OTHER PUBLICATIONS

Esko et al, Variational Formulation of Open-Ended Coaxial Line in Contact with Layered Biological Medium, Oct. 1998, IEEE Transactions on Biomedical Engineering vol. 45, p. 1241-1248.*

(Continued)

*Primary Examiner* — Brian Szmal
*Assistant Examiner* — Huong Nguyen
(74) *Attorney, Agent, or Firm* — Harrington & Smith

(57) ABSTRACT

The invention relates to a method for measuring tissue edema. By a method in accordance with the invention an electromagnetic probe (24) is placed on the skin, and the capacitance of the probe is proportional to the dielectric constant of the skin and subcutaneous fat, which is proportional to the water content of the skin. The edema is scored by measuring the capacitance of the electromagnetic probe, so called open-ended coaxial cable, at a high frequency, approximately 20-500 MHz.

20 Claims, 3 Drawing Sheets

(56) References Cited

U.S. PATENT DOCUMENTS

Figure 1:
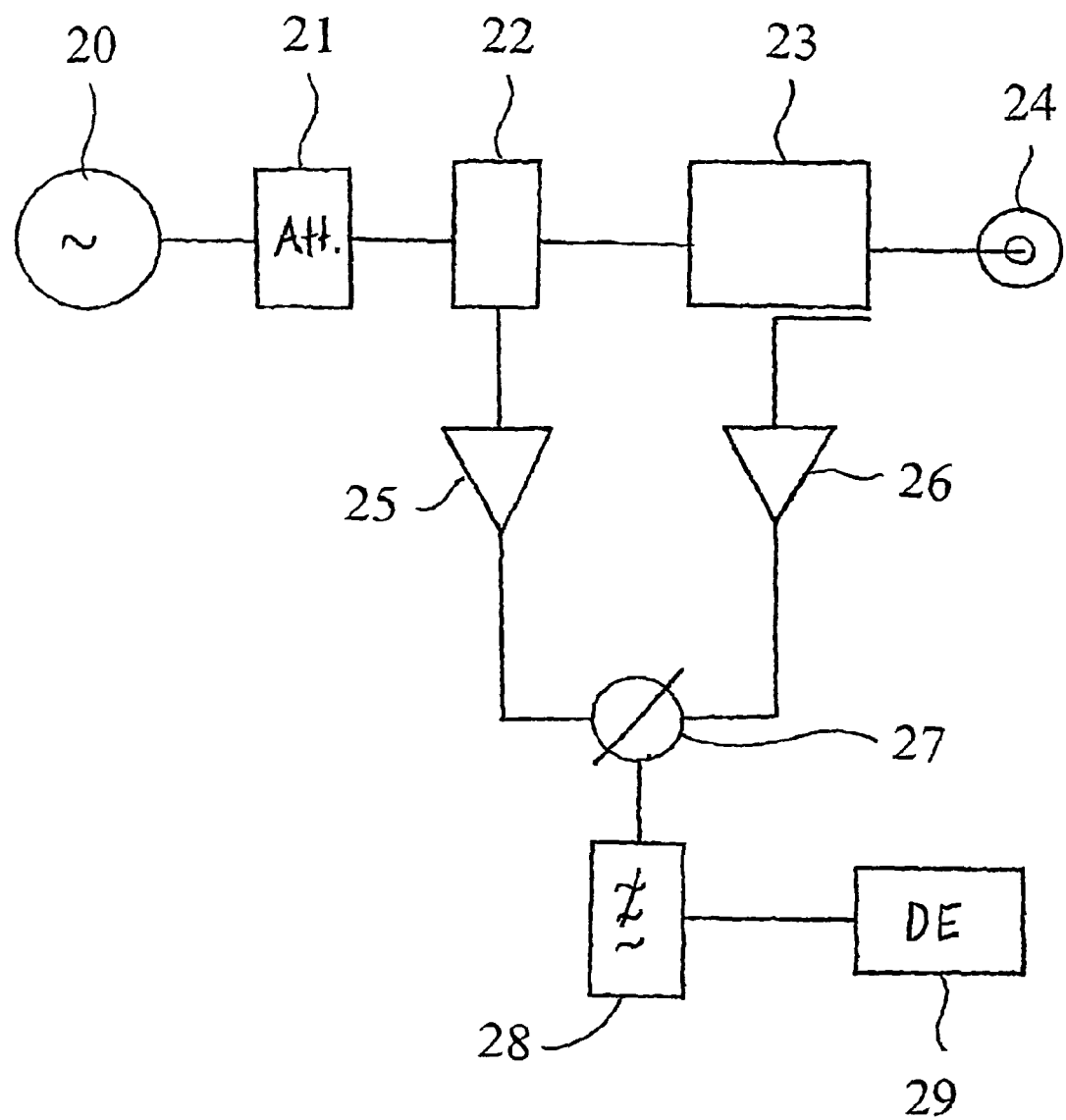

| | | | |
|---|---|---|---|
| 3,742,936 A | 7/1973 | Blanie et al. | 128/2.1 Z |
| 3,750,649 A | 8/1973 | Severinghaus | 128/2.1 Z |
| 3,789,834 A * | 2/1974 | Duroux | 600/407 |
| 3,851,641 A * | 12/1974 | Toole et al. | 600/529 |
| 3,871,359 A | 3/1975 | Pacela | 128/2.1 Z |
| 3,894,532 A | 7/1975 | Morey | 128/2.1 Z |
| 3,949,736 A | 4/1976 | Vrana et al. | 128/2.1 Z |
| 4,008,712 A | 2/1977 | Nyboer | 128/2.1 Z |
| 4,013,065 A | 3/1977 | Copeland et al. | 128/2 R |
| 4,116,231 A | 9/1978 | Matsuo | 128/2.1 Z |
| 4,240,445 A | 12/1980 | Iskander et al. | 128/804 |
| 4,364,008 A * | 12/1982 | Jacques | 324/636 |
| 4,640,290 A * | 2/1987 | Sherwin | 600/382 |
| 4,793,362 A | 12/1988 | Tedner | 128/734 |
| 4,819,648 A | 4/1989 | Ko | 128/653 |
| 4,860,753 A * | 8/1989 | Amerena | 600/306 |
| 4,911,175 A | 3/1990 | Shizgal | 128/734 |
| 4,918,375 A * | 4/1990 | Malicki et al. | 324/642 |
| 5,063,937 A | 11/1991 | Ezenwa et al. | 128/723 |
| 5,086,781 A | 2/1992 | Bookspan | 128/734 |
| 5,280,429 A | 1/1994 | Withers | 364/413.15 |
| 5,738,107 A | 4/1998 | Martinsen et al. | 128/734 |
| 5,749,369 A | 5/1998 | Rabinovich et al. | 128/734 |
| 5,833,686 A * | 11/1998 | Zhao | 606/34 |
| 6,125,297 A | 9/2000 | Siconolfi | 600/547 |
| 6,292,690 B1 | 9/2001 | Petrucelli et al. | 600/547 |
| 6,339,722 B1 | 1/2002 | Heethaar et al. | 600/547 |
| 6,370,426 B1 * | 4/2002 | Campbell et al. | 600/547 |
| 6,823,212 B2 * | 11/2004 | Pinyayev | 600/547 |
| 7,297,123 B2 | 11/2007 | Sonis | 600/590 |
| 2003/0015024 A1 * | 1/2003 | Campbell et al. | 73/73 |
| 2003/0214312 A1 | 11/2003 | Khatchatrian et al. | 324/692 |
| 2004/0186392 A1 | 9/2004 | Ward et al. | 600/547 |
| 2006/0200033 A1 | 9/2006 | Keren et al. | 600/504 |

FOREIGN PATENT DOCUMENTS

| | | | |
|---|---|---|---|
| GB | 2 272 526 A | | 5/1994 |
| WO | WO 99/08597 | * | 2/1999 |
| WO | WO-0079255 A1 | | 12/2000 |

OTHER PUBLICATIONS

Esko et al, Penetration of Electromagnetic Fields of an Open-Ended Coaxial Probe between 1 MHz and 1 GHz in Dielectric Skin Measurements, 1999, Phys. Med. Biol. 44, p. N169-N176.*

Esko et al, Measurement of Dielectric Properties of Subcutaneous Fat with Open-Ended Coaxial Sensors, 1998, Phys. Med. Biol. 43, p. 475-485.*

Kao, H. Pin, et al., "Correlation of Permittivity and Water Content During Cerebral Edema", IEEE Transactions on Biomedical Engineering, vol. 46, No. 9, Sep. 1999.

Zuhdi Lababidi, D. A. Ehmke, Robert E. Durnin, Paul E. Leaverton and Ronald M. Lauer; "The First Derivative Thoracic Impedance Cardiogram," *Circulation—Journal of the American Heart Association*, 1970; 41: 651-658.

Jan Nyboer, Marian M. Kreider and Leonard Hannapel; "Electrical Impedance Plethysmography: A Physical and Physiologic Approach to Peripheral Vascular Study," *Circulation—Journal of the American Heart Association*, 1950, 2: 811-821.

Sherwood, et al. "Methodological Guidelines for Impedance Cardiography," *Psychophysiology*, vol. 27, No. 1: 1-23.

H. H. Woltjer, H. J. Bogaard and P. M. J. M. de Vries; "The technique of impedance cardiography," European Heart Journal (1997) 18, 1396-1403.

* cited by examiner

METHOD FOR MEASURING OF EDEMA

CROSS-REFERENCE TO RELATED APPLICATIONS

This is a continuation-in-part application of International Application No. PCT/FI02/00234 filed Mar. 21, 2002, which is hereby incorporated by reference in its entirety; and which claims priority to Finnish Patent Application No. 20010601 filed Mar. 23, 2001.

The present invention relates to a method for measuring tissue edema.

Edema in biological material is a state where more water is accumulated in the tissue than in a normal physiological situation. An accumulation of extra water in soft organs leads to an increase in volume. Water in tissue is either intracellular or extracellular. It is carried to the tissue in the blood, the plasma in the blood is continually exchanging with the water in the tissue.

Edema develops if more water is imported to tissue than exported from it. The reason for edema may be a constriction or a thrombus in the vein transporting the blood from the tissue, the increased permeability of plasma from the blood vessels, inflammation of the tissue or dilation of vessels caused by an internal or external reason. Edema is always a serious symptom of a disturbance in blood circulation, increased permeability of vessels or inflammations. Therefore the measurement of edema is of great medical significance.

Edema in limbs is usually measured by using a tape measure. U.S. Pat. No. 5,891,059 describes a method where limb edema is detected by measuring the circumference of the limb and comparing the result against a control value. The difference between the readings describes the value of edema in the patient. The increase of circumference describes then the general limb edema, but does not give knowledge of the edema in difference tissue formations. The increase in tissue volume caused by edema can be detected by medical imaging devices such as computer tomography or MRI. However, these methods are expensive.

Edema can also be measured by weighting the body mass. It can also be followed up by fluid balance calculation where all the liquids taken internally are measured and compared with natural liquid losses.

The most common way to assess skin edema is to press the skin by hand for a while and then to check how much it takes for the skin to even-out again. For normal skin it takes a few seconds but for swollen skin it may take even tens of seconds. U.S. Pat. No. 5,957,867 describes a method where the limb is set on a plate where a moveable rod is connected. The rod is pushed through a hole in the plate onto the skin surface and is then pushed further to a predefined distance. At the same time a system attached to the device measures the pressure profile, which is proportional to the rate of edema. Obviously these methods are not accurate nor give any specific knowledge of the tissue.

According to well-known techniques the dielectric constant of biological tissues has been measured with electrodes placed inside the tissue. The benefit of these methods is the close contact of the electrodes with the target volume. The measurement is made by sending an oscillating electromagnetic field into the tissue. From the interaction of the electric field and the tissue the dielectric properties of the tissue can be calculated as a function of frequency. The result of the dielectric measurement is usually a value measured by one or more frequencies. It is proportional to the complex permittivity, dielectric constant or conductivity of the tissue. The disadvantage of these techniques is that the electrodes, usually 2-4, have to be place invasively into the tissue, hence damaging the tissue.

These kinds of methods are used to measure the dielectric properties of tissues, which are proportional to the water content. When the water content of tissue is changing within the normal limits it is not an edema e.g. increased water content, but normal physiological functioning.

U.S. Pat. No. 5,580,727,0 describes an electric measuring device for brain edema, by which the intracellular edema in brain cells can be monitored for hours or days. The device is electrically insulated from the mains voltage and feeds an AC current of 1 mA at a frequency of 200 Hz to the outer electrodes of a four-electrode system on the skin surface. The middle electrodes are located inside the scull. The disadvantage of this method is the surgery required The object of the present invention is to provide a method, which obviates the shortcomings of the present systems. Furthermore the object of the invention is to provide an advantageous method for measuring a local tissue edema from the skin surface of person non-invasively and continuously or instantly. It is a further objective to provide a method, which does not impose any restrictions on the measurement site or the type of edema.

The object of the invention is achieved by the method, which is described in the claims.

In a method in accordance with the invention an electromagnetic probe is placed in contact with the skin, in which case the capacitance of the probe is proportional to the dielectric constant of the underlying tissue, which is further proportional to the water content of skin, and the edema is scored by measuring the capacitance of the probe at a high frequency, approximately 20-500 MHz. The probe is an open-ended coaxial cable.

In the method a coaxial electrode is placed on the skin, and an electromagnetic field, with a high frequency (20-500 MHz), is transmitted through the skin and subcutaneous fat tissue. The field that is reflected back from the tissue is measured. From the reflected field the dielectric constant of the skin can be calculated. The dielectric constant is proportional to the relative water content of the skin, which increases as the edema develops. The measured value is partly affected by the dielectric constant of the subcutaneous fat tissue, which is low because of its low water content. The skin becomes thicker as the edema increases and the fat tissue moves further from the probe with the result that its effect is decreased. Therefore the two effects of the edema, the increased dielectric constant of skin and the thickening of the skin change the measured value in the same direction.

An essential feature of the invention is the high radio frequency (approximately 20-500 MHz), because at these frequencies the electric field penetrates deeply into the skin and subcutaneous fat tissue. At lower frequencies the electric field is concentrated on the superficial layers of the skin and the measurement of edema is not possible.

Substantial benefits are obtained with the present invention. Edema can be monitored locally from the surface of the skin by placing the electrode on the measuring site for a long time. Edema can be monitored without any invasive operation of a part of the measuring device. Measurements taken by the device according the invention do not disturb the edema in any way. With the invention the assessment of the effect of medical proceedings, liquid treatments, medication and physical treatments on the edema can be improved.

In an advantageous application of the invention the measurement is made manually with only a few seconds measurement. In this way a local edema can be rapidly detected. In another advantageous application of the invention the measurement is made by placing the probe on the skin for a long time for instance hours or days, with an attachment, such as a strap. In this way the edema can be monitored continuously for a long time.

In a further advantageous application of the invention the device operates only at one exactly pre-selected frequency. The electrical properties of a tissue are dependent on the frequency and therefore reliable and comparable information from the tissue can be obtained by measuring with only one pre-selected frequency.

In a further advantageous application of the invention the edema is measured from the upper layers of the skin by using 20-50 MHz radio frequencies, in which case the electric field is concentrated on these layers. In this way the upper layers of the skin can be measured without any delay and reliably.

In a further advantageous application of the invention the edema is measured from deeper layers of the skin by using 50-500 MHz radio frequencies, in which case the electric field penetrates deeply into the skin tissue (dermis) and the underlying subcutaneous fat tissue. In this way the deeper layers of the skin and the underlying fat tissue can be measured without any delay and reliably.

Figure 2:
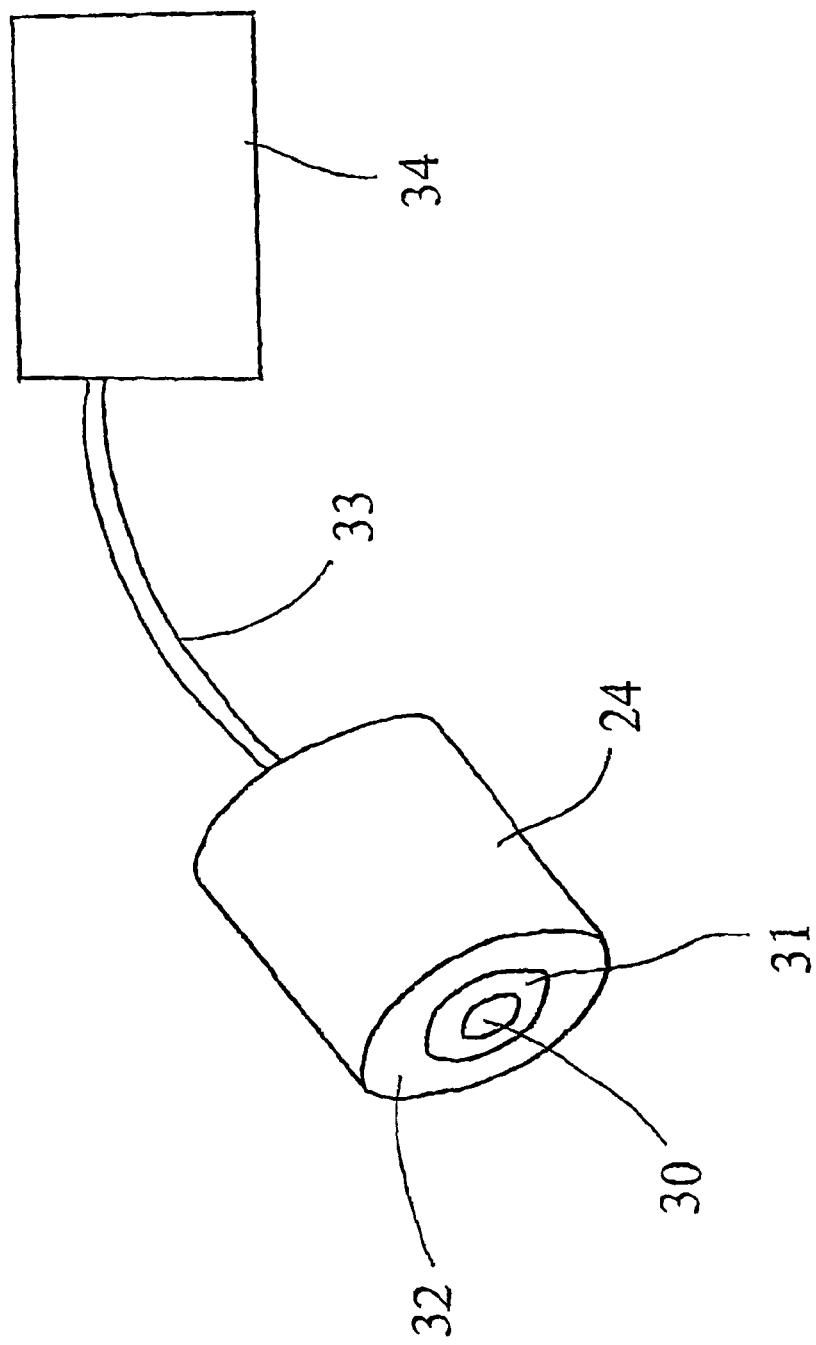
Figure 3:
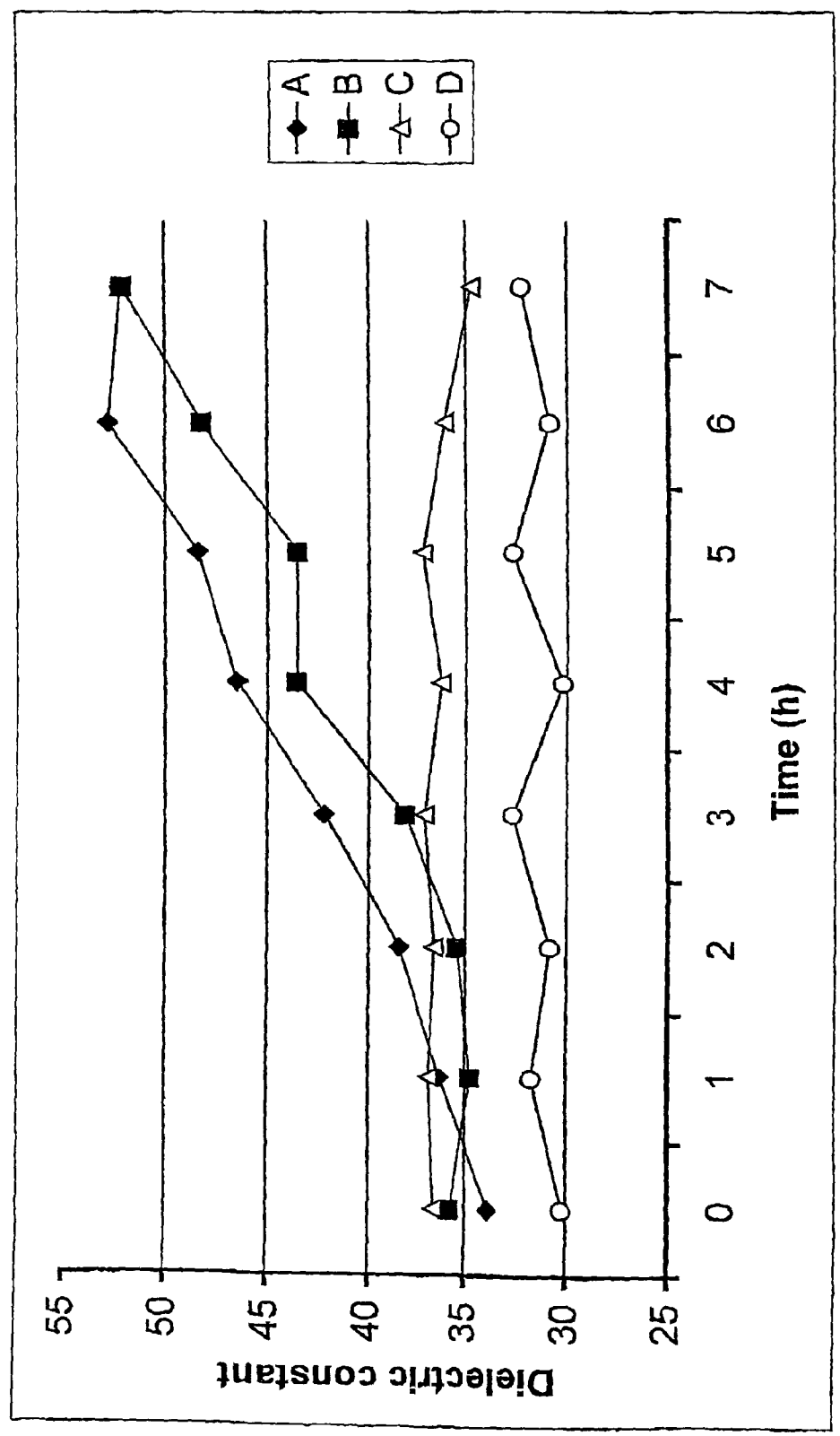

The invention will now be described in greater detail with reference to the accompanying drawings, where FIG. 1 shows a block diagram showing the operation of the device, FIG. 2 shows the probe connected to the electronic unit by a coaxial cable, FIG. 3 shows the result of an example case of developing edema in pig skin caused by controlling blood circulation at sites A and B. Sites C and D are the controls.

FIG. 1 shows an probe including an oscillator 20, an attenuator 21, a power splitter 22, a directional coupler 23, a probe 24, amplifiers 25 and 26, a phase detector 27, a low pass filter 28 and a digital electronic unit 29. The block diagram in FIG. 1 can vary in different applications of the method. It may also be utilised in other ways.

FIG. 2 shows the probe 24, including an inner electrode 30, a Teflon insulator 31, an outer electrode 32, a coaxial cable 33 and an electronic unit 34 comprising the components of FIG. 1 excluding the probe 24.

An essential feature of the device according to the invention is that the coaxial probe is large enough, in order for the electric field to penetrate up to the subcutaneous fat tissue. The distance between the two electrodes of the probe should be about 2-10 mm.

The device operates so that the sinusoidal high frequency (20-500 MHz) signal from the oscillator 20 is led through the attenuator 21, power splitter 22 and directional coupler 23 to the probe 24. The signal is reflected back from the probe. Part of this reflected signal is led through the directional coupler 23 to the amplifier 26 and further to one input of the phase detector 27. The signal coming straight from the oscillator 20 is led through the power splitter 22 to the other input of the phase detector 27. The output from the phase detector is led to the low pass filter 28, whose output is a DC voltage proportional to the capacitance of the probe 24. This voltage is further led to the digital electronic unit, where it is AD-converted, scaled and recorded.

The output of the phase detector 27 after the low pass filtering is proportional to the phase difference, which is only dependent on the capacitance of the probe 24. The device operates on a single precisely set frequency and therefore the result is only dependent on the dielectric properties of the tissue and not on the conductivity.

The probe 24 is connected to the directional coupler 23 via the coaxial cable so that the signal is connected to the inner conductor of the cable and further to the inner electrode 30 of the probe 24, and the ground signal is connected to the outer conductor of the cable and further to the outer electrode 32 of the probe 24.

FIG. 1 shows only one example of the high frequency implementation of the method. It is made using known techniques. The essential feature is that the capacitance of the probe is measured at a high frequency 20-500 MHz.

The high frequency unit of the device, comprising of parts 20-27, is realised using standard radio techniques. In practice this means that the components are connected to each other with microstrip lines which have a defined impedance, for instance 50 ohms. Therefore the same signal line can propagate signals in both directions simultaneously. The fact that the dimensions of the circuit are small compared to the wavelength does not in any way affect the operation of the high frequency components.

An essential feature of the high frequency unit is that the signal amplitude in both inputs of the phase detector 27 is so high that the detector operates in a saturated state. Therefore the phase detector 27 measures only the phase difference of the incoming signals. This phase difference is proportional to the capacitance of the probe 24 and fiber proportional to the dielectric constant of the tissue. The dielectric constant is dependent on the water content of the skin.

Another essential feature of the high frequency unit is the attenuator 21 between the oscillator 20 and the power splitter 22. Its purpose is to prevent the access of the signal reflected from the probe to the amplifier 25. Under the influence of the amplifier the signal reflected from the probe goes twice through the attenuator 21 when propagating to the input of the amplifier 25. Therefore, if the attenuation of the attenuator 21 is for instance 6 dB, the total attenuation of this signal is 12 dB, which is adequate.

FIG. 3 shows as an example case of a measurement of a developing edema in pig skin, where by controlling the blood circulation a local edema is caused at sites A and B. Sites C and D are the controls. It can be seen that at the sites with edema (A and B) the dielectric constant is increased by over 40% compared to the baseline. At the control area (sites C and D) where the developing edema does not exist the measured values remain unchanged. The measurement reacts rapidly to the edema, even before it is noticeable for instance by finger pressure.

The present invention is not restricted to the aforementioned advantageous application, but can be utilised in other forms within the limits of the idea of the invention as defined by the claims.

The invention claimed is:

1. A method for measuring tissue edema, comprising:
placing an open-ended coaxial probe on a skin surface;
transmitting an electromagnetic field through the skin surface;
measuring a capacitance of the probe, wherein the measured capacitance of the probe is proportional to a dielectric constant of skin tissue and subcutaneous fat tissue, which is further proportional to a water content of the skin tissue and the subcutaneous fat tissue, the probe having two concentric electrodes separated by a distance configured such that the electromagnetic field penetrates past the skin tissue to the subcutaneous fat tissue underneath the skin tissue, wherein said distance is 6 mm to 10 mm, wherein said distance is along a radial direction, wherein the two concentric electrodes comprise an inner electrode and outer electrode, and wherein said distance is from an outer edge of the inner electrode to an inner edge of the outer electrode;
scoring the edema by measuring the capacitance of the probe at a frequency of 20-500 MHz.

2. A method according to claim 1, in which
the measurement is made manually and takes between one and ten seconds.

3. A method according to claim 1, in which
for the measurement the probe is secured on the skin surface by a strap attachment, for hours or days, in which case the edema can be monitored continuously.

4. A method according to claim 1, in which
the edema of an upper part of a dermis is measured using a frequency of 20-50 MHz, in which case an electric field is concentrated in the upper part of the dermis.

5. A method according to claim 1, in which
the edema of a lower part of a dermis and the underlying subcutaneous fat tissue is measured using a frequency of 50-500 MHz, in which case an electric field penetrates deeply into the lower part of the dermis and the underlying subcutaneous fat tissue.

6. A method according to claim 1 wherein a measured value of the edema is based, at least partially, on the dielectric constant of the subcutaneous fat tissue.

7. A method according to claim 1 wherein the measuring of the capacitance of the probe at the high frequency further comprises measuring the edema of a dermis.

8. A method according to claim 1 wherein the tissue edema of a dermis and of the underlying subcutaneous fat tissue is measured.

9. A method according to claim 1 wherein the two electrodes of the open-ended coaxial probe comprise an outer electrode and an inner electrode, wherein the outer electrode comprises a circular shape, wherein the inner electrode comprises a circular shape, wherein the outer electrode surrounds the inner electrode, wherein an insulator is between the outer electrode and the inner electrode, wherein the insulator surrounds the inner electrode, and wherein the distance between the inner electrode and the outer electrode is 7-10 mm.

10. A method as in claim 1 wherein the open-ended coaxial probe comprises a single open-ended coaxial probe, and wherein the electromagnetic field penetrates through skin layers including a dermis, wherein the electric field further penetrates beyond the skin layers and penetrates into the subcutaneous fat tissue, wherein a phase difference of a reflected electromagnetic field is measured, and wherein a water content of the skin corresponds to the phase difference.

11. A device for measuring tissue edema, which device includes
an open-ended coaxial probe configured to be placed on a skin surface during the measurement wherein a capacitance of the probe is proportional to a dielectric constant of the skin tissue and subcutaneous fat tissue, which is further proportional to a water content of the skin tissue and the subcutaneous fat tissue,
a plurality of high frequency components configured to measure the capacitance of the probe, wherein the plurality of high frequency components are arranged to measure the capacitance of the probe at a first range of 20-50 MHz, wherein the first range corresponds to a measure of an upper part of a dermis,
wherein the plurality of high frequency components are arranged to measure the capacitance of the probe at a second range of 50-500 MHz, and wherein the second range corresponds to a measure of a lower part of the dermis and the subcutaneous fat tissue,
a calculating unit configured to calculate the dielectric constant and the tissue edema, and
the probe having two concentric electrodes separated by a distance, the distance between the two electrodes of the probe configured such that the electromagnetic field penetrates past the skin tissue and into the subcutaneous fat tissue, wherein said distance is 6 mm to 10 mm, wherein said distance is along a radial direction, wherein the two concentric electrodes comprise an inner electrode and outer electrode, and wherein said distance is from an outer edge of the inner electrode to an inner edge of the outer electrode.

12. A device according to claim 11, in which the device is arranged to measure only on a single precisely set frequency.

13. A device according to claim 11, in which the high frequency unit comprises an oscillator, a power splitter, and an attenuator connected between the oscillator and the power splitter, wherein attenuator is configured to prevent access of a signal reflected from the electromagnetic probe.

14. A device according to claim 13 wherein attenuator is configured to prevent access of a signal reflected from the electromagnetic probe to an amplifier, and wherein under the influence of the amplifier the signal reflected from the electromagnetic probe goes twice through the attenuator when propagating to an input of the amplifier.

15. A device according to claim 11 wherein a measured value of the tissue edema is based, at least partially, on the dielectric constant of the subcutaneous fat tissue.

16. A device according to claim 11 wherein the high frequency unit is configured to measure the capacitance of the probe at the first range of 20-50 MHz and at the second range of 50-500 MHz for measuring the tissue edema of the upper part of the dermis, and the lower part of the dermis and the subcutaneous fat tissue, respectively.

17. A device according to claim 11 wherein the device is configured to measure the tissue edema of the dermis and of the underlying subcutaneous fat tissue.

18. A device according to claim 11 wherein the two electrodes of the open-ended coaxial probe comprise a first electrode and a second electrode, wherein the first electrode comprises a circular shape, wherein the second electrode comprises a circular shape, wherein the first electrode surrounds the second electrode, wherein an insulator is between the first electrode and the second electrode, wherein the insulator surrounds the second electrode, and wherein said distance between the first electrode and the second electrode is 8-10 mm.

19. A method for measuring tissue edema comprising:
placing an open-ended coaxial probe on a skin surface, wherein the probe comprises two electrodes, wherein the two electrodes are concentric, wherein a distance separating the two electrodes of the probe is 6-10 mm, wherein said distance is along a radial direction, wherein the two concentric electrodes comprise an inner electrode and outer electrode, and wherein said distance is from an outer edge of the inner electrode to an inner edge of the outer electrode;
generating a first signal from an oscillator, wherein a frequency of the first signal is 20 to 500 MHz;
transmitting a first portion of the first signal to the probe and through the skin tissue and subcutaneous fat tissue;
receiving a reflected signal from the skin tissue and subcutaneous fat tissue through the probe;
leading the reflected signal to a first input of a phase detector;
transmitting a second portion of the first signal to a second input of the phase detector, operating the phase detector in a saturated state, wherein signal amplitudes from the reflected signal and the second portion of the first signal form the saturated state;

measuring a phase difference between the reflected signal and the second portion of the signal;

calculating a dielectric constant from the phase difference;

calculating a water content of the skin tissue and the subcutaneous fat tissue based on the dielectric constant; and detecting edema based on, at least partially, the water content.

20. A method according to claim 19 wherein the two electrodes of the open-ended coaxial probe comprise an outer electrode and an inner electrode, wherein the outer electrode comprises a circular shape, wherein the inner electrode comprises a circular shape, wherein the outer electrode surrounds the inner electrode, wherein an insulator is between the outer electrode and the inner electrode, wherein the insulator surrounds the inner electrode, and wherein the insulator has a thickness of 7-10 mm.

* * * * *